United States Patent [19]

Ozaki et al.

[11] Patent Number: 5,209,826

[45] Date of Patent: May 11, 1993

[54] METHOD OF SEPARATING SESAMIN AND EPISESAMIN

[75] Inventors: Tatsuhiko Ozaki; Yasunari Hoshii; Hirokazu Matsueda, all of Aichi, Japan

[73] Assignee: Takemoto Yushi Kabushiki Kaisha, Aichi, Japan

[21] Appl. No.: 920,653

[22] Filed: Jul. 28, 1992

Related U.S. Application Data

[63] Continuation of Ser. No. 661,061, Feb. 26, 1991, abandoned.

[51] Int. Cl.$^5$ .................. B01D 3/12; B01D 3/38; C12P 7/64
[52] U.S. Cl. ..................... 203/38; 203/79; 203/80; 435/126; 435/134
[58] Field of Search ............... 203/38, 79, 80, DIG. 6; 435/126, 134; 260/420

[56] References Cited

U.S. PATENT DOCUMENTS

| | | | |
|---|---|---|---|
| 2,467,904 | 4/1949 | Omohundro et al. | 549/435 |
| 2,837,534 | 6/1958 | Tracy | 549/435 |
| 4,705,690 | 11/1987 | Brand et al. | 426/590 |
| 4,708,820 | 11/1987 | Namiki et al. | 549/464 |
| 4,710,228 | 12/1987 | Seaborne et al. | 426/89 |
| 4,844,721 | 7/1989 | Cox et al. | 55/85 |
| 4,916,066 | 4/1990 | Akimoto et al. | 435/134 |
| 5,010,004 | 4/1991 | Kosagi et al. | 435/134 |
| 5,089,404 | 2/1992 | Matsumoto et al. | 435/134 |

OTHER PUBLICATIONS

Shimizu et al., "Production of C-20 Polyunsaturated Fatty Acids by Fungi", ISF, JOCS World Congress, 1988, pp. 1000–1006.

Shimizu et al., "Production of Dihomo-γ-linolenic Acid by *Mortierrella Alpina* 1S-4", JAOCS, vol. 66, No. 2, Feb. 1989, pp. 237–241.

*Primary Examiner*—Virginia Manoharan
*Attorney, Agent, or Firm*—Heller, Ehrman, White & McAuliffe

[57] ABSTRACT

A steam stripping fraction of sesame seed oil with increased concentration of sesamin and episesamin is used in a molecular distillation process to obtain a fraction containing more than 70 weight % of sesamin and episesamin. The steam stripping fraction is preferably obtained by a steam stripping process wherein the temperature ($t°$ C.) of the sesame seed oil and the pressure (P mmHg) for the process are such that $\{(4.24 \times 10^3)/(9.41 - \log P)\} - 273 \leq t \leq 280$ and $0.5 \leq P \leq 20$.

2 Claims, No Drawings

METHOD OF SEPARATING SESAMIN AND EPISESAMIN

This is a continuation of parent application Ser. No. 07/661,061 filed Feb. 26, 1991, now abandoned.

BACKGROUND OF THE INVENTION

This invention relates to a method of separating sesamin and episesamin.

Sesame seeds contain about 0.3–0.5 weight % of d-sesamin. Unrefined sesame seed oil obtained by squeezing sesame seeds contains about 0.5–1.0 weight % of d-sesamin. If such unrefined sesame seed oil is processed with activated clay or the like, not only d-sesamin but also episesamin which is generated by optical isomerization of d-sesamin come to be contained.

It has long been known that sesamin and episesamin have strong cooperative effects on pyrethrin-type insecticides. More recently, it was reported (ISF-JOCS World Congress, (1988)) that linear polyunsaturated fatty acids such as arachidonic acid (cis-5, 8, 11, 14-eicosatetraenoic acid) and cis-5, 8, 11, 14, 17-eicosapentaenoic acid can be synthesized enzymatically in the presence of fungi (hyphomycetes). It was also reported (JAOCS 66, 237–241, (1989)) that the presence of sesamin and episesamin adversely affects the production of arachidonic acid in a production process by using fungi, while there results an accumulation of a significant quantity of dihomo-γ-linolenic acid (cis-8, 11, 14-eicosatrienoic acid) which is a precursor of arachidonic acid and is considered to be difficult to synthesize enzymatically. It is now understood that this is due to the so-called enzyme inactivation effect of sesamin and episesamin, that is, the peculiar inhibitive effect of sesamin and episesamin on enzymatic dehydrogenation reaction by which arachidonic acid is generated from dihomo-γ-linolenic acid. Eicosapolyenoic acids such as dihomo-γ-linolenic acid and arachidonic acid are precursors of prostaglandins, thromboxanes, leucotriens, etc. which are all important biological regulators.

It is therefore an object of the present invention to provide a method of efficiently separating from sesame oil sesamin and episesamin which exhibit strong cooperative effects as mentioned above and participate in the biosynthesis of biological regulators.

Many methods of using various organic solvents to directly extract sesamin and episesamin from sesame seed oil have been attempted, including a method of using methanol as organic solvent/water (U.S. Pat. No. 2,467,903), a method of using acetone/water (U.S. Pat. No. 2,467,904), a method of using cooled petroleum ether (U.S. Pat. No. 2,557,956), a method of using acetonitrile (U.S. Pat. No. 2,786,063), and a method of using γ-butylolactone (U.S. Pat. No. 2,837,534). These prior art methods, however, have the following disadvantages: (1) since the obtained extract contains a significant amount of sesamolin and glyceride in addition to sesamin and episesamin, the concentration of sesamin and episesamin in the extract is low; (2) since the concentration of sesamin and episesamin in sesame seed oil is at most about 1 weight %, a large amount of solvent must be used; (3) the cost of energy becomes quite high for distilling away the organic solvent which has been used; and (4) since organic solvents cannot be completely removed from sesame seed oil, the processed sesame seed oil, if such an organic solvent has been used, cannot serve any longer as food for hygienical reasons.

Besides the above, there has also been proposed a method of using an organic solvent for direct extraction of sesamin and episesamin from sesame seed oil and thereafter repeating recrystallization processes with the extracted liquid to refine and separate sesamin and episesamin (JAOCS, 31, 302 (1954)). This method overcomes the first of the four aforementioned disadvantages but the rest of the problems remain unsolved.

Still another method has been proposed (JAOCS 33, 197 (1956)) according to which sesamin and episesamin are directly extracted from sesame seed oil by using a molecular distillation apparatus. An apparatus for molecular distillation, however, involves a high installation cost and consumes a large amount of energy. Since sesame seed oil containing at most only about 1 weight % of sesamin and episesamin is directly fed to such an apparatus, the cost per unit amount of sesamin and episesamin obtained turns out to be extremely high. Moreover, if such sesame seed oil is directly fed into such an apparatus and is subjected to high temperatures for a long period of time, it produces conspicuously rancid flavored substances due to thermal decomposition of unsaturated glycerides which are contained or thermal polymerization of unsaturated fats. As a result, the sesame seed oil, after undergoing such a process, cannot serve as food any longer.

SUMMARY OF THE INVENTION

It is therefore an object of the present invention to eliminate the disadvantages of the prior art method of separating sesamin and episesamin.

The present invention is based on the inventors' discovery as a result of their diligent studies in view of the above and other objects that good results can be obtained if a steam stripping fraction of sesame seed oil is used for molecular distillation to obtain a fraction containing more than 70 weight % of sesamin and episesamin (hereinafter referred to as sesamins).

DETAILED DESCRIPTION OF THE INVENTION

This invention relates to a method of separating sesamins by blowing steam into a sesame seed oil to thereby collect a steam stripping fraction with a high concentration of sesamins and by carrying out molecular distillation of this steam stripping fraction to thereby obtain a fraction containing more than 70 weight % of sesamins. The steam stripping process and the molecular distillation process may be carried out continuously. Alternatively, the fraction from the steam distillation process may be stored first and then used for the molecular distillation process later.

For the steam stripping process according to the present invention, use may be made of sesame seed oil obtainable by various known methods such as squeezing sesame seeds or extracting by using a solvent such as n-hexane. In particular, if sesame seeds are not roasted and if unrefined sesame seed oil obtained by squeezing and compressing such seeds is subjected to deacidification, decolorization and deodorization processes to obtain refined sesame seed oil, it is advantageous to use sesame seed oil after deacidification and decolorization in a refining process because, as will be explained below, the step of steam stripping can be carried out as a part of the deodorization process. If use is made of sesame seed oil after a decolorization step in a refining process wherein activated clay or the like is used, sesamolin changes into other substances by the catalytic effect of activated clay or the like. As a result, one can obtain sesame seed oil not containing sesamolin, which has a similar vapor pressure as sesamins. A fraction with a higher concentration of sesamins can thus be obtained.

In the steam stripping process according to the present invention, steam is blown into sesame seed oil of an aforementioned kind to distil away its volatile components and to thereby obtain a fraction. According to a preferred embodiment of the invention, this process may be carried out under a condition described below to obtain a fraction with a high concentration of sesamins:

$$\{(4.24 \times 10^3)/(9.41 - \log P)\} - 273 \leq t \leq 280$$

where t is the temperature in °C. of the sesame seed oil and P is the pressure in mmHg and such that $0.5 \leq P \leq 20$.

In other words, a preferred steam stripping process is carried out by blowing steam into sesame seed oil under a condition of high temperature and high degree of vacuum to distil away its volatile components and to collect a fraction with a high concentration of sesamins but it is important that the oil temperature and the pressure must satisfy the condition given above. The minimum temperature of the sesame seed oil which can satisfy the condition given by the formula above is about 180° C. if P is 1 mmHg, about 210° C. if P is 5 mmHg, about 230° C. if P is 10 mmHg and about 250° C. if P is 20 mmHg, but maximum temperature allowed according to the formula above is always 280° C. independently of the degree of vacuum (or P). If the temperature exceeds 280° C., thermal deterioration of sesame seed oil and trans-isomerization of unsaturated glycerides contained therein are likely to occur. More preferably, the steam stripping process should be carried out with the minimum temperature of sesame seed oil about 10° C. higher than the minimum temperature given by the formula above and P in the range of 2–6 mmHg.

The fractions obtained by the steam stripping process described above can be roughly divided as follows: (1) low-boiling point fraction of which the principal components include aliphatic ketones and aldehydes with 2–12 carbon atoms and lower aliphatic acids and terpene-type hydrocarbons with 8 carbon atoms or less, (2) middle-boiling point fraction of which the principal components include higher aliphatic acids such as palmitic acid, oleic acid and linoleic acid, and which also includes sterols, and (3) high-boiling point fraction of which the principal components include mono-glycerides and di-glycerides of higher aliphatic acids. Sesamins are generally collected as a fraction with boiling point between those of (2) and (3) above and are contained in such a fraction by 10–35 weight %.

The aforementioned steam stripping process can be carried out by using a deodorization device for edible oil and fats for the purpose of removing off-flavored substances, free aliphatic acids, etc. Examples of such a deodorization device which is used for the refinement of vegetable oils such as bean oil, rice oil and rape seed oil include the batch type, the semi-continuous type and the continuous type. More particularly, use may be made of a Girdler-type continuous and semi-continuous deodorization device, a Desmet-type continuous deodorization device and a Campro Flow-type continuous deodorization device. If a Girdler-type semi-continuous deodorization device is used for the aforementioned steam stripping process, sesamins are collected in the booster drain in the vacuum system but this booster drain corresponds to a fraction somewhere between the aforementioned middle-boiling point and high-boiling point fractions. When the deodorization device is used for steam stripping, a middle-boiling point fraction is collected in a collection tank in its exhaust system and the middle-boiling point fraction thus collected in the collection tank becomes separated into a lower layer of water and an upper layer of aliphatic acids. This water layer is either suspended or emulsified, and deposits sink to its bottom part. If the water layer, together with such deposits, is subjected to a centrifugal separation process, a solid containing 10–30 weight % of sesamins is obtained. The high-boiling point fraction, on the other hand, condenses inside the deodorization tower and is collected as shell drain but this shell drain hardly contains any sesamins. This means that it is most advantageous to make use of the booster drain and the aforementioned solid when the steam stripping process is carried out by using a Girdler-type semi-continuous deodorization device.

The molecular distillation process according to the present invention is a process whereby a steam stripping fraction thus obtained and having an increased concentration of sesamins is used for molecular distillation such that a fraction containing more than 70 weight % of sesamins is obtained.

A steam stripping fraction obtained by the aforementioned steam stripping process may be directly used for the next molecular distillation process. Since such a steam stripping fraction contains, besides sesamins, higher aliphatic acids such as oleic acid and linoleic acid, their mono- and di-glycerides, phenol compounds and sterols as well as a small amount of triglycerides, the aliphatic acids may be preliminarily removed from the fraction by low-pressure or vacuum distillation before the fraction is used for the molecular distillation process. According to a preferred embodiment of the present invention, lower alcohol with 1–4 carbon atoms such as methanol and ethanol is reacted with the steam stripping fraction in the presence of an esterification catalyst so as to preliminarily esterify the higher aliphatic acids in the fraction before it is used for the molecular distillation process. This makes it easier, in the initial stage of the molecular distillation process, to distil away the esterified low-boiling point components and reduces the load on the exhaust for the vacuum system.

It is similarly preferable to react the fraction from the steam stripping process with lower alcohol in the presence of an ester exchange catalyst to cause an ester exchange reaction between the glycerides of aliphatic acids in the fraction and the lower alcohol prior to the molecular distillation process. This has the effect of reducing the amount of various low-boiling point by-products generated by the thermal decomposition of glycerides during the molecular distillation and also of preventing the materials produced by thermal polymerization of glycerides from becoming attached as sludge onto the evaporation surface of the molecular distillation apparatus. Moreover, the low-boiling point components which participated in the ester exchange reaction are easier to remove. As a result, it becomes possible in this manner to obtain a principal fraction with high concentration of sesamins efficiently and at a high yield.

Prior art molecular distillation apparatus may be used for the molecular distillation process of this invention. As particular examples, falling film molecular distillation apparatus and centrifugal molecular distillation apparatus may be mentioned. The oil temperature for the molecular distillation process is normally 320° C. or below and preferably 300° C. or below. The degree of vacuum (measured by pressure) is normally 0.5 mmHg or below and preferably 0.3 mmHg or below.

Although a principal fraction containing sesamins by more than 70 weight % can be obtained by the molecular distillation process, a more highly concentrated principal fraction containing more than 90 weight % of sesamins can be obtained by more finely cutting the fraction. If the principal fraction thus obtained is recrystallized by using an organic solvent such as acetone/methanol, ethanol and chloroform, it is also possible to obtain a very highly concentrated fraction containing more than 99 weight % of sesamins.

In what follows, the invention will be described by way of examples but these examples are intended to be merely illustrative and not as limitative.

Preparation of Sesame Seed Oil

Roughly refined sesame seed oil obtained by using an expeller according to an ordinary method to squeeze Chinese sesame seeds (with oil content of 51.2 weight %) was deacidified and washed with water. Thereafter, 0.5 weight % of activated clay was added and a decolorization process was carried out at 80°–85° C. and 70 mmHg for 30 minutes and a filter press was used to separate the activated clay filtrate to prepare decolorized sesame seed oil. This sesame seed oil was used in the following series of tests.

Test 1

Use was made of a Girdler-type semi-continuous deodorization apparatus with a 6-step tray and the decolorized sesame seed oil was introduced at the rate of 1000 kg/hour into a decolorization tower kept in a vacuum condition of 2.5 mmHg. The oil temperature was raised to 160° C. at the first tray by indirect heating by steam and to 235° C. at the second tray by electrical heating. At the third through fifth trays, steam with vapor pressure of 6 kg/cm² was blown in for steam stripping at the rate of about 1 weight % of the oil to be processed. The oil temperature was 230° C. at the third tray, 225° C. at the fourth tray and 220° C. at the fifth tray. At the sixth tray, the oil temperature was reduced to 40° C. by means of cooling water while about 0.1 weight % of nitrogen gas (with respect to the oil being processed) was blown in. At the sixth tray, the cooled steam-stripped sesame seed oil was introduced to a drop tank outside the deodorization tower and after it was taken out of the system by means of an exhaust pump, it was filtered by means of a sparkler-type filtering device to get refined sesame seed oil. The acid value of this refined sesame seed oil was less than 0.01, its color was light yellow, no unpleasant odor was sensed and there was no problem in using it as food.

After this process was continued for 24 hours, the fraction which was accumulated at the bottom of the deodorization tower (shell drain=Fraction A), the fraction which was accumulated at the booster of the vacuum system (booster drain=Fraction B) and the solid which was obtained by centrifugal separation of the lower, water layer inside the collection tank of the exhaust system (=Fraction C) were collected and analyzed. The results of this analysis are shown in Table 1.

TABLE 1

| Fraction | Higher aliphatic acids (wt %) | Glyceride (wt %) | Sesamins (wt %) | Other (wt %) |
|---|---|---|---|---|
| A | 2 | 97.5< | 1> | 0.5> |
| B | 47 | 19 | 31 | 3 |
| C | 63 | 2 | 25 | 10 |

For Table 1, the analysis was by high-speed liquid chromatography. The test conditions were as follows:
Column: Develosil ODS-5 (by Nomura Kagaku)
Column size: 4.6 mm$\phi$ × 150 mm
Solvent Methanol/water = 70/30 (V/V)
Flow rate: 1 ml/min
Detection: UV (290 nm)
For sesamins, the total for sesamin and episesamin is shown.

Test 2

Fraction B (340 g) obtained in Test 1 was directly set in a falling film molecular distillation apparatus for molecular distillation. The results are shown in Table 2, in which Fractions 4, 5 and 6 embody the present invention.

TABLE 2

| Fraction | Oil Temp. (°C.) | Degree of Vacuum (mmHg) | Fraction mass (g) | Sesamins (wt %) |
|---|---|---|---|---|
| 1 | 200 | 0.1 | 32 | 0 |
| 2 | 215 | 0.2 | 31 | 0 |
| 3 | 230 | 0.2 | 31 | 31 |
| 4 | 245 | 0.3–0.4 | 25 | 70 |
| 5 | 260 | 0.2 | 26 | 85 |
| 6 | 275 | 0.25 | 34 | 90 |
| Residue | — | — | 161 | trace |

(For sesamins, the total for sesamin and episesamin is shown.)

Test 3

Fraction B (320 g) obtained in Test 1, methanol (450 g) and p-toluene sulfonic acid (3 g) were placed inside a flask with reflux condenser for an esterification reaction for one hour with heating and a return current at the boiling point of methanol. Next, methanol was distilled away at reduced pressure to obtain 330 g of reaction product.

Molecular distillation was carried out as in Test 2 with 313 g of this reaction product. The results are shown in Table 3, in which Fractions 3, 4 and 5 embody the present invention.

TABLE 3

| Fraction | Oil Temp. (°C.) | Degree of Vacuum (mmHg) | Fraction mass (g) | Sesamins (wt %) |
|---|---|---|---|---|
| 1 | 230 | 0.20–0.25 | 180 | 0 |
| 2 | 245 | 0.25 | 4 | 49 |
| 3 | 260 | 0.3 | 16 | 70 |
| 4 | 275 | 0.3 | 17 | 77 |
| 5 | 300 | 0.3 | 44 | 86 |
| Residue | — | — | 51 | 1> |

(For sesamins, the total for sesamin and episesamin is shown.)

Test 4

Fraction B (470 kg) obtained in Test 1, methanol (800 kg) and concentrated sulfuric acid (4 kg) were placed inside a reaction tank for an esterification and ester exchange reaction at 70° C. for 5 hours. After an aqueous solution of sodium hydroxide was added to neutralize the reaction system, methanol was distilled away at reduced pressure. After warm water (100 liter) was added to the content and vigorously stirred, it was left quietly and the resultant water layer was removed. After this process was repeated twice, a reaction product (452 kg) was obtained by dehydration at reduced pressure.

By using 452 kg of this reaction product with a falling film molecular distillation apparatus, Fraction F1 (270 kg) and Residue R1 (182 kg) were obtained by molecular distillation under the conditions of feed rate=180 liter/hour, oil temperature=180° C. and pressure =0.18 mmHg. The principal component of Fraction F1 was higher aliphatic acid methyl esters and no sesamins were detected therein.

Next, Residue R1 (182 kg) was used for molecular distillation by a falling film molecular distillation apparatus under the conditions of feed rate=120 liter/hour, oil temperature=290° C. and pressure=0.11 mmHg to obtain Fraction F2 (117 kg) and Residue R2 (30 kg) with a loss of 35 kg. Fraction F2 embodies the present invention, containing sesamins by 85 weight %. No sesamin analogues were detected in Residue R2.

Test 5 (Comparison)

Decolorized sesame seed oil (2200 g) was placed inside a falling film molecular distillation apparatus and a fraction (31 g) and a residue (1663 g) were obtained by molecular distillation under the conditions of feed rate =13 ml/min, oil temperature=300° C. and pressure=0.25-0.30 mmHg with a loss of 506 g. The results of analyses on the fraction and the residue thus obtained are shown in Table 4. The principal component of the residue included triglycerides and their decomposition products. A large amount of free aliphatic acids was contained and there was a conspicuous odor of aldehyde. It could not be offered as food without any further processing.

TABLE 4

|  | Appearance | Odor | Sesamins (wt %) | Acid Value |
|---|---|---|---|---|
| Fraction | Soft solid | significant odor of aldehyde | 23 | 93.5 |
| Residue | yellow-brown oil | significant odor of aldehyde | trace | 25.3 |

Test 6 (Comparison)

Decolorized sesame seed oil was placed inside a vacuum distillation apparatus provided with a steam inlet and was gradually heated while steam was blown in and the interior pressure was maintained at 5 mmHg. Effusion started when the oil temperature reached about 150° C. The heating was continued and steam distillation was discontinued when the oil temperature was 200° C. The results of analysis on the fraction thus obtained are given below in units of weight %.
Lower aldehydes and ketones: 65
Lower aliphatic acids: 18
Higher aliphatic acids: 14
Hydrocarbons: 1>
Others with unknown structure: 2<
No sesamins were detected at all.

These test results confirm that the present invention provides a method of obtaining sesamins with high purity by separating them from sesame seed oil without making the sesame seed oil unusable as food after the separation.

The foregoing description of preferred embodiments of the invention has been presented for purposes of illustration. It is not intended to be exhaustive or to limit the invention to the precise form disclosed. Many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that those modifications and variations which may be apparent to persons skilled in the art be included within the scope of the invention.

What is claimed is:

1. A method of separating sesamin and episesamin, said method comprising the steps of blowing steam into a sesame seed oil by a steam stripping process to thereby collect a steam stripping fraction with an increased concentration of sesamin and episesamin, and of carrying out molecular distillation of said steam stripping fraction to thereby obtain a product fraction containing more than 70 weight % of sesamin and episesamin, said step of blowing steam being carried out under such conditions of the temperature (t° C.) of said sesame seed oil and the pressure (P mmHg) for said process that:

$$\{(4.24 \times 10^3)/(9.41 - \log P)\} - 273 \geq t \geq 280$$

and $$0.5 \leq P \leq 20.$$

2. The method of claim 1 further comprising the step of reacting said steam stripping fraction with alcohol with 1-4 carbon atoms in the presence of a catalyst for esterification or ester exchange reaction between glycerides of aliphatic acids contained in said steam stripping fraction and the alcohol before said step of molecular distillation.

* * * * *